(12) United States Patent
Martin et al.

(10) Patent No.: US 6,202,897 B1
(45) Date of Patent: Mar. 20, 2001

(54) UNIT DOSE LIQUID DISPENSING AND PACKAGING FOR DENTAL APPLICATION

(75) Inventors: Thomas W. Martin, Little Canada; John M. Horn, Woodbury, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/139,441

(22) Filed: Aug. 25, 1998

(51) Int. Cl.$^7$ ...................................................... B67D 5/42
(52) U.S. Cl. ........................... 222/386; 433/90; 206/269; 206/63.5
(58) Field of Search .................................. 222/386, 325, 222/326, 327, 80, 90, 82, 83; 433/89, 90; 206/308, 309, 63.5, 368, 369; 211/85.13, 74, 69.5; 401/135, 142; 604/68, 72, 275

(56) References Cited

U.S. PATENT DOCUMENTS

| | | |
|---|---|---|
| D. 377,216 | 1/1997 | Mark .................................. D24/152 |
| D. 377,525 | 1/1997 | Mark .................................. D24/152 |
| 550,763 | 12/1895 | Osmun . |
| 2,616,423 * | 11/1952 | Kurkjian ............................. 604/200 |
| 3,221,360 | 12/1965 | Seeman .............................. 15/537 |
| 3,230,574 | 1/1966 | Kershaw ............................ 15/563 |
| 3,345,674 | 10/1967 | Groft ................................... 15/563 |
| 3,459,483 | 8/1969 | Brastad .............................. 401/131 |
| 3,464,775 | 9/1969 | Beal .................................... 401/199 |
| 3,818,911 | 6/1974 | Fournier ............................ 128/269 |
| 3,900,954 * | 8/1975 | Dragan ................................ 32/60 |
| 4,573,818 * | 3/1986 | Kodera ............................... 401/131 |
| 4,578,055 | 3/1986 | Fischer .............................. 604/2 |
| 4,892,481 | 1/1990 | Kopunek et al. . |
| 4,969,816 | 11/1990 | Drumm .............................. 433/90 |
| 4,997,371 | 3/1991 | Fischer .............................. 433/90 |
| 5,033,629 * | 7/1991 | Caine ................................. 211/69.5 |
| 5,097,853 | 3/1992 | Nehashi ............................. 132/320 |
| 5,100,320 | 3/1992 | Martin et al. ...................... 433/90 |
| 5,123,766 * | 6/1992 | Babiak ............................... 401/180 |
| 5,195,663 | 3/1993 | Martin et al. ...................... 222/327 |
| 5,199,567 | 4/1993 | Discko, Jr. . |
| 5,246,371 | 9/1993 | Fischer .............................. 433/217.1 |
| 5,269,684 | 12/1993 | Fischer .............................. 433/90 |
| 5,286,257 | 2/1994 | Fischer .............................. 604/82 |
| 5,297,698 | 3/1994 | Martin ............................... 222/95 |
| 5,358,349 | 10/1994 | Burroughs et al. ................ 401/184 |
| 5,445,523 | 8/1995 | Fischer et al. .................... 433/90 |
| 5,626,473 | 5/1997 | Muhlbauer et al. .............. 433/89 |
| 5,743,436 | 4/1998 | Wilcox et al. .................... 222/137 |
| 5,816,804 * | 10/1998 | Fischer .............................. 433/90 |
| 6,059,570 * | 5/2000 | Dragan et al. .................... 433/80 |

FOREIGN PATENT DOCUMENTS 19647529   5/1998   (DE) .
WO 97/26041   7/1997   (WO) ........................... A61M/37/00

\* cited by examiner

Primary Examiner—Henry J. Recla
Assistant Examiner—Huyen Le
(74) Attorney, Agent, or Firm—James D. Christoff

(57) ABSTRACT

An nozzle for storage and application of liquid dental material, such as primer or adhesive, to a preparation site at a patient's teeth, gums or mouth. The nozzle includes a hollow nozzle for containing the liquid dental material. The hollow nozzle can include a flocked, open tip through which the liquid dental material is dispensed. The nozzle also includes a storage block having a plurality of cavities formed therein. A plurality of hollow nozzles can be inserted into the cavities to form substantially air-tight seals between the open tips of the hollow nozzles and the exterior of the cavities. An end of the hollow nozzles opposite from the open tip and exposed above the block includes a breakable seal. Accordingly, the hollow nozzles can be stored in the block for an extended period of time. To apply the liquid dental material to a preparation site, an applicator can be attached to the end of the hollow nozzle exposed above the block. The applicator is adapted to break the breakable seal and force the liquid dental material from the interior of the hollow nozzle through the open tip and onto an application site.

34 Claims, 5 Drawing Sheets

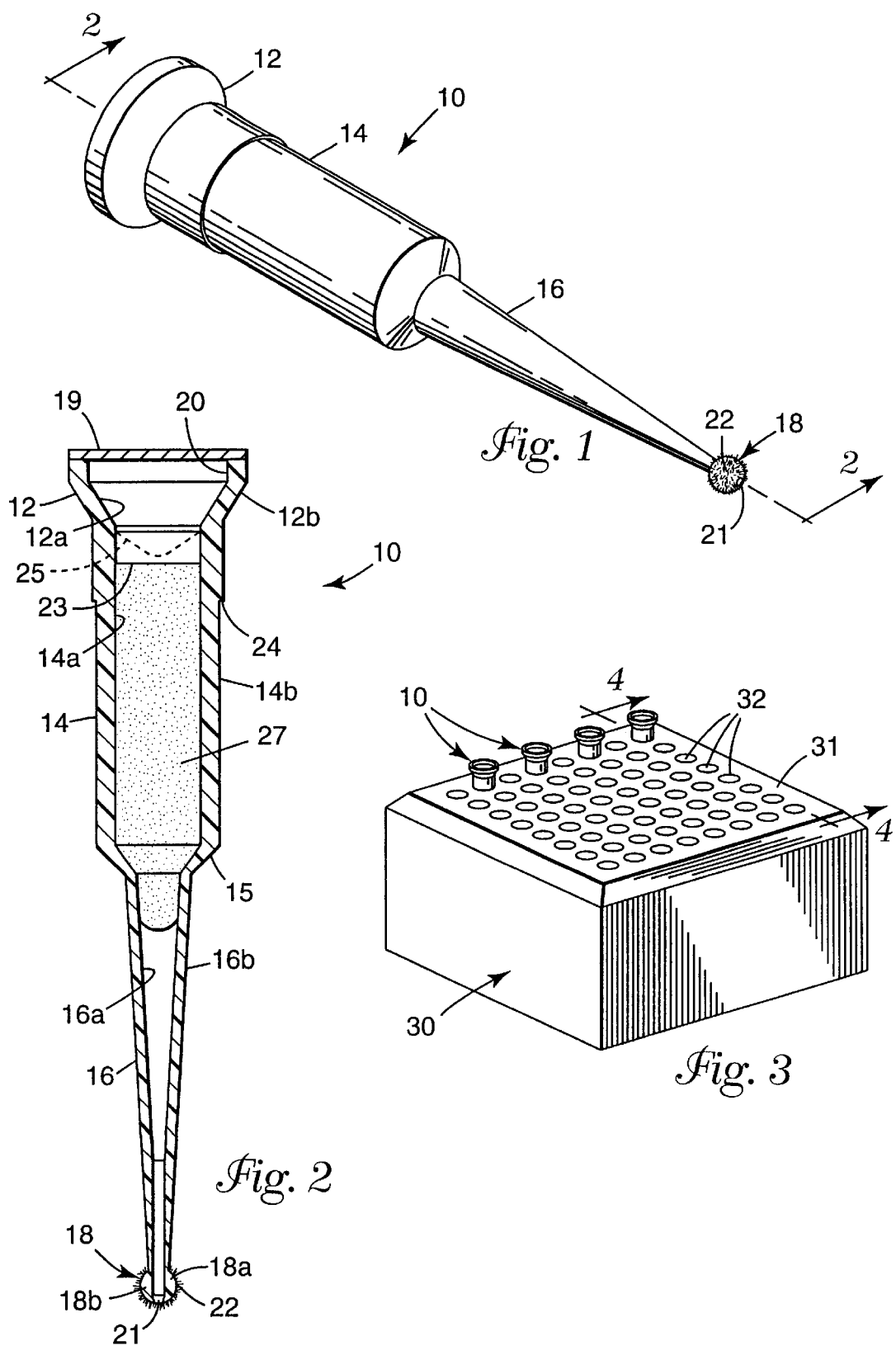

UNIT DOSE LIQUID DISPENSING AND PACKAGING FOR DENTAL APPLICATION

TECHNICAL FIELD

The present invention relates to a manner of packaging liquid material, such as dental liquid, from which the liquid material can be dispensed and applied directly to a surface, such as to the surface of a tooth. More specifically, the present invention relates to a dispensing tip and tip storage device within which liquid material can be stored and from which unit doses of liquid material can be dispensed and applied to a surface.

BACKGROUND

In performing various dental procedures, dental professionals routinely apply various liquid materials to preparation sites on the teeth, gums and/or other areas of the mouth of a patient. Such materials include primers, adhesives and other liquid dental preparations.

To the degree possible, storage, preparation and use of these materials should be carried out in an environment and manner consistent with good infection control practices. Thus, the manner of packaging and storing liquid dental materials should accommodate the need to dispense the dental material by such a process, including the equipment and devices for dispensing, and to maintain an appropriate level of sterility of the material over time, especially when multiple doses of material are stored in bulk. Typically, this means that the reusable devices and products are disinfected with cold sterilants between uses. Certain applying equipment or devices are usually sterilized in an autoclave between uses.

Additionally, in some cases, dental liquids need to be stored in a way to limit the permeation of solvents from the dental liquid through its container. For example, most dental adhesive systems today contain solvents to increase their wettability so that they are easier to apply to a tooth surface. During storage, however, it is important to prevent substantial evaporation of the solvent from the liquid material in order to protect the effectiveness of the liquid material. A vessel made of material having a limited permeability to solvents can be used, such as made from relatively thick plastic, or a foil pouch can be provided about the stored quantity of material. Sealable plastic containers having presealable caps or other closures are common from which multiple doses can be dispensed. Foil pouches typically contain single doses either directly therein, or within a unit dose container sealed therein.

An advantage of a resealable container having multiple doses is that it would typically require less storage space as compared to single dose packages. Single dose packages, such as contained within foil pouches, require substantially greater space than the volume of liquid dental material contained within each package.

There exist a number of different devices and methods for storing and applying such liquid dental materials. One common procedure for storing and applying liquid dental materials involves dispensing the dental material from a sealable bulk vial into a well which can be either reusable or disposable. The sealable vial maintains sufficient sterility and avoids excessive evaporation of solvents. Once the liquid material is placed into the well, a brush or other fiber tipped applicator is dipped into the well so that the fiber tip of the applicator can retain a quantity of the liquid material. The material is then coated onto the tooth surface or other preparation site. Often, additional coats of the material are required and so the applicator will be re-dipped into the well so that additional coats can be applied. If the material is light cured, such as for example those materials commercially available under the trade designation "3M Single Bond Dental Adhesive System" from Minnesota Mining & Manufacturing Company of St. Paul, Minn., care must be taken to shield the well from light exposure during this procedure. After the procedure, the fiber tip of the applicator and the well, if disposable, are disposed of. Typically, the entire brush or the brush handle; the well, if non-disposable; and the bulk vials are disinfected with a liquid disinfectant.

A number of brush types are known for use as dental applicators and can be used with the above procedure. A relatively standard type brush is simply a small paint brush comprising bristles fixed with an elongate handle. Another type of brush includes relatively small fibers adhered to and extending radially from a spherical tip portion of an elongate brush handle. Such a brush is known as a flocked tip brush comprising nonabsorbent fibers between which liquid can be held in suspension, an example of which is commercially available under the trade designation "Microbrush" from Microbrush Corporation of Clearwater, Fla. Yet another type of brush comprises a reusable brush handle connected with a replaceable brush tip. The tip may be a standard bristle type brush or a flocked tip. A replaceable flocked tip brush is described in copending U.S. design patent application Ser. No. 29/070,517 and in U.S. design Pat. No. 377,216 to Mark. This type of brush allows disposal of the brush tip and sterilization and re-use of the handle.

Regardless of the type of brush used with the above described procedure, however, the procedure has a number of drawbacks. First, spillage is possible either in filling the well from the bulk vial or in applying the material to the preparation site. Second, the lid or cap of the bulk vial must be handled which can cause contamination, requires two hands and can be difficult with gloves on. Third, two hands are also required for both filling the well and applying the liquid. Fourth, because the material must first be dispensed from a bulk source into the well before application, the procedure can be relatively time consuming. Fifth, if the well is not disposable, the well must be cleaned and the well, brush, applicator handle and bulk vial all must be disinfected. Thus, cleanup can also be time consuming. Sixth, if the bulk vial is opaque, it can be difficult to determine how many applications of the liquid material are left before additional material must be supplied. Finally, gloves make all parts of the procedure which require handling or manipulation of items difficult. Gloves are typically worn during dental procedures for infection control.

Another system for storage, dispensing, and applying liquid dental material delivers the material via a bulk syringe source having multiple doses of material. A bulk quantity of liquid dental material is provided in a re-usable syringe and dispensed through its hollow dispensing tip. This approach allows for direct application of the material to a tooth without the need to use a disposable or reusable dispensing well. However, the entire syringe must be disinfected after each use. Also, if the bulk syringe source is opaque, it can be difficult to determine how many applications of the liquid material remain. Care must also be taken to effectively reseal the syringe after each use to maintain the material's effectiveness.

A third type of system for applying liquid dental material uses unit dose packaging. This type of system uses a disposable package containing approximately enough liquid dental material for a single application. An example is the delivery system commercially available under the trade designation "Optibond Solo" from Kerr Company of Orange, Calif. A small plastic container having dental material therein is provided within a foil pouch. This process requires opening the sealed foil pouch and subsequently breaking a unit dose plastic container to access the liquid dental material. Then, a brush or other fiber tipped applicator can be used as above to apply the material to a preparation site. This eliminates the need for using a well and dispensing the material into the well.

Because the package is sealed, there is no need for a separate, sealable bulk vial for infection control and to prevent excessive evaporation of solvents. Also, this system avoids clean-up requirements of a separate bulk vial and well. However, the system still requires two hands and spillage can occur if the package is set down on a dental tray or in transfer of the material from the package to the preparation site with the applicator. Additionally, opening the packages can be difficult while wearing gloves. Further, as above, storage of the separate unit dose packages can take up a relatively large amount of space.

SUMMARY OF THE INVENTION

The present invention includes a package for effective and space efficient storage, dispensing and application of liquid material which reduces the likelihood of spillage during application, can reduce the amount of time required for preparation and cleanup, and can allow application of liquid material using only a single hand and in a substantially "no-touch" process. The package comprises a plurality of dispensing and applying nozzles that are provided in a storage block. Although not so limited, the present invention is designed to be particularly applicable for storing, dispensing and applying dental liquids to a dental preparation site, such as a tooth surface.

In accordance with one aspect of the present invention, a hollow nozzle is provided having an open tip through which the liquid material is dispensed, and a liquid applicator mechanism at the open tip to retain a small quantity of the liquid material for application of the material at a preparation site.

The nozzle preferably contains a unit dose of liquid material so that a new nozzle can be used for each application of the material at different preparation sites. Moreover, each nozzle is disposable after a dispensing and applying process is completed. The liquid application mechanism of each tip may comprise any known or developed technique for dispersing liquid material about the tip as supplied from a nozzle outlet and for holding or suspending a small quantity of liquid material and by which liquid can be substantially evenly applied to a surface. Preferably, the nozzle tip is flocked to provide small radially extending bristles for this purpose. The hollow nozzle is preferably designed for attachment to a driver for controlling dispensing of the liquid material from the hollow nozzle. In dentistry, the use of a disposable nozzle means that only the driver needs to be disinfected after an application. Moreover, no bulk vial or well or other equipment is needed to perform the process.

In accordance with another aspect of the present invention, a packaging system includes a plurality of nozzles containing liquid material from which the material can be dispensed. The nozzles are stored in a storage block that effectively caps each of the nozzles in a convenient, easy access way. Each hollow nozzle is removably engaged within a cavity of the packaging block to form a seal having a suitable limited solvent permeability. This allows liquid dental material, for example, to be stored in the hollow nozzle for an extended period of time.

Preferably, the capping device is a block having a plurality of cavities formed therein. A filled nozzle can be inserted into each of the plurality of cavities and be stored in the block until used. Moreover, after usage, the depleted nozzles can be stored by the storage block until disposal of the entire package is desired. More preferably, each cavity forms with each nozzle plural seals for limiting solvent evaporation and thus increasing shelf life. Also, each nozzle preferably includes a liquid application mechanism at its open tip to facilitate application of the liquid material, and each cavity is designed to accommodate the liquid application mechanism within the cavity. Where the liquid application mechanism is a flocked tip or other bristled tip, the cavity is sized at its internal end to surround the tip without crushing it. An internal seal is preferably created by an intermediate surface portion of each nozzle within a cavity, and an outer seal is preferably also provided at the surface of the storage block by another surface portion of each nozzle. To accomplish the internal and outer seals, each nozzle may be tapered to converge toward its tip and the storage block cavities may each be comprised of an inner and outer bore portions, with the inner bore portion being of a smaller dimension so that the tapered surface of a nozzle can contact the cavity at a transition between the outer and inner bore portions and at the edge of the outer bore portion with an external surface of the storage block. Preferably, the transition comprises an annular step surface between cylindrical outer and inner bore portions. The nozzle preferably also includes a flange sealing surface to provide the outer seal by contacting the external surface of the storage block surrounding its respective cavity.

BRIEF DESCRIPTION OF THE DRAWINGS

FIG. 1 is a perspective view of a nozzle for use in storage, dispensing and application of liquid material in accordance with the present invention.

FIG. 2 is a cross-sectional view of the nozzle shown in FIG. 1 taken along section line 2—2 of FIG. 1.

FIG. 3 is a perspective view of a packaging and storage block containing a plurality of nozzles of the type shown in FIG. 1 in accordance with the present invention.

DETAILED DESCRIPTION

Figure 4:
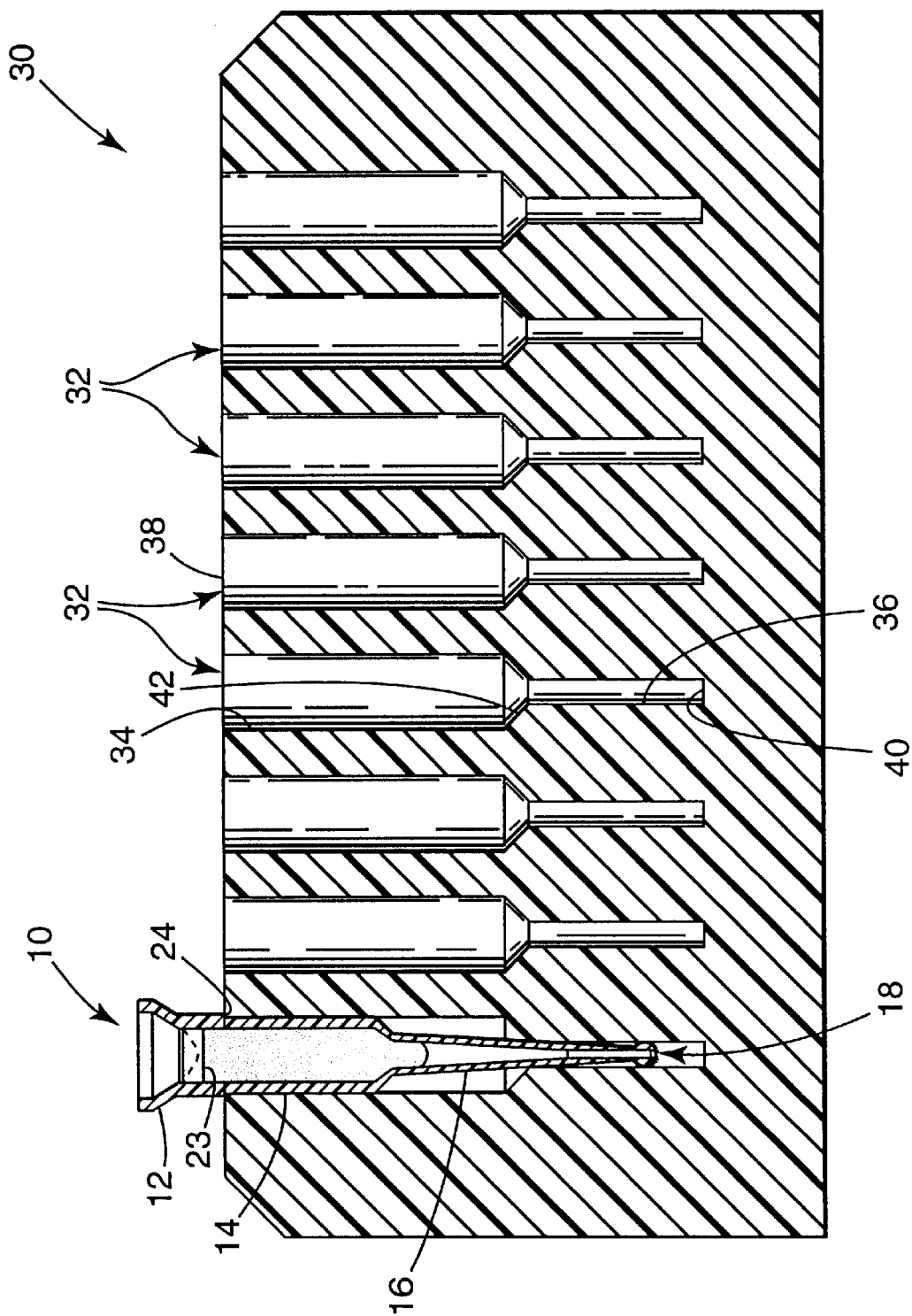
FIG. 4 is a sectional view of the packaging and storage block shown in FIG. 3 taken along section line 4—4 thereof.

In FIG. 1, a storage, dispensing and applicator nozzle 10 is illustrated which is specifically designed for, but not limited to, use in storing, dispensing and applying liquid dental material to a dental preparation site. A dental preparation site can be any surface of a patient's mouth, such as gums or teeth, to which a dental material is to be applied. Moreover, the present invention is designed for the dispensing and application of liquid dental material to such a preparation site. As discussed above in the Background section, in performing various dental procedures, dental professionals routinely apply various liquid materials to preparation sites on the teeth, gums and/or other areas of the mouth of a patient. Such materials include primers, adhesives and other liquid dental materials. Where a tooth is to be filled, for example, it is common practice to fill the preparation with a dental composite material. The composite material is typically held in place by an adhesive, which itself may require the application of an etchant directly to the tooth surface to improve adhesion. Many manners of applying and curing liquid etchants, adhesives and composite materials are known. Nozzle 10, in accordance with the present invention, is designed specifically for its benefits in storing, dispensing and applying such liquid dental materials directly to a tooth surface. It is understood, however, that the nozzle 10 may be used for storing, dispensing and applying other liquid materials directly to the surface of an object.

Nozzle 10 can provide for the space efficient storage of liquid dental material in accordance with good infection control practice. Nozzle 10 can also minimize the likelihood of spillage during application, can reduce the amount of time required for preparation and cleanup, and can allow application of liquid dental material using only a single hand and in a substantially "no-touch" process. For other non-dental applications, the same advantages can apply.

As shown in FIG. 1, nozzle 10 comprises a number of portions of different dimension that generally are reduced in size from one end to another. Preferably, nozzle 10 is overall generally conical as comprised of plural cylindrical portions, including, as shown in FIG. 2, a relatively wide upper flange section 12, an intermediate liquid storage section 14, and a lower liquid dispensing section 16 which converges to a tip 18. The nozzle 10 need not be generally conical or comprise cylindrical portions, but preferably at least leads to a tip having a size and shape suitable for applying liquid to a particular surface. That is, the size and shape may differ depending on the particular application. The non-tip end is preferably sized and shaped for connection to a driver or other dispense causing means (examples of which are described below), which again may differ depending on any particular application.

Preferably, nozzle 10 is formed of plastic or other polymeric material, such as polypropylene, for example, so as to facilitate manufacturing, such as by injection molding. It is, however, also contemplated to form nozzle 10 or portions thereof from other materials with suitable barrier properties. The choice of material for the nozzle 10 or any portion thereof may depend on the particular application, such as for example based upon characteristics of a material such as flexibility, deformability, heat resistance, chemical resistance or reactiveness, water absorption, burst strength, light transparency (for any given wavelength), etc. Furthermore, the internal or external surfaces may be treated, coated or otherwise comprise different materials to facilitate the needs of any particular application. Examples of suitable materials are disclosed in U.S. Pat. No. 5,100,320 to Martin et al., the entire disclosure of which is incorporated herein by reference.

As noted above, nozzle 10 is hollow and, thus, defines an internal cavity that preferably extends entirely through the nozzle 10. Specifically, flange section 12, storage section 14, dispensing section 16 and tip 18 each include an internal section 12a, 14a, 16a and 18a, respectively, corresponding to respective external sections 12b, 14b, 16b and 18b. As shown, the internal sections 12a, 14a and 16a generally also correspond to the external shapes of their respective sections 12b, 14b and 16b. This also may be varied for a particular application. Sections 12a, 14a and 16a may be independently coated or treated.

Flange section 12 of nozzle 10 has a relatively wide inlet 20 at an upper end thereof. A breakable or removable end-seal is preferably provided by a seal 19 at inlet 20 for sealing inlet 20 during storage. The seal 19 preferably comprises a foil/film laminate material that can be heat sealed to the perimetric edge defining the inlet 20 as are commonly known for providing container end-seals, but may comprise any known or developed material. A preferred material is a heat sealable foil/film laminate material commercially available from Rexam Company of Mount Holly, N.J. under the trade designation D-041-38. Seal 19 may comprise other suitable material and may be attached about the perimeter of inlet 20 by heat sealing, with adhesive, or by other means so as to provide a substantially airtight seal between the interior of nozzle 10 and the exterior thereof at inlet 20. Additionally, seal 19 is preferably puncturable to allow access to the interior of nozzle 10, as is described in greater detail below. Otherwise, a tab or other feature may be added to the seal 19 to facilitate easy removal thereof from the inlet 20. It is also contemplated that the seal be provided by other mechanisms such as a removable plastic cap.

Flange section 12 is preferably designed for interfitting with a driver (described below) and is thus preferably sized and shaped to be quickly connectable and disconnectable with such a driver. The nozzle 10 should be connectable in a way that permits access to the driver for entering the nozzle 10 through inlet 20. A releasable quick connection is preferred that will longitudinally fix the nozzle in position to such a driver, but permit the nozzle 10 to be disconnected by a radial movement. The enlarged size of the flange section 12 relative to the size of the adjacent intermediate storage section 14 accommodates this preference.

Both the interior flange section 12a and exterior flange section 12b preferably taper down into the liquid storage section 14. For sealing the nozzle 10 in a preferred package construction discussed below, a shoulder 24 is provided along the surface of the exterior storage section 14b. The extent of the shoulder may be minimal to provide an effective sealing surface. If sealing by the shoulder 24 is not needed, the shoulder may be eliminated or merely provided by any structure as a limiting surface (i.e. a structure that doesn't need to surround the nozzle 10 since sealing by it is not required). With a cylindrical section 14, as shown, the shoulder 24 is preferably annular to also create a sealing surface. Another tapered portion 15 connects liquid storage section 14 with dispensing section 16. The portion 14 (and the taper within section 12 near section 14) may alternatively be a stepped portion or may instead provide for a smoother transition between the respective sections, which may be defined by straight or curved surfaces. The more abrupt transition provided by a sharp taper or a step can be beneficial for maintaining a quantity of more viscous liquid material 27 above the tip 18 during storage. Section 16, including its interior dispensing section 16a and exterior dispensing section 16b, preferably gradually converges toward tip 18. Though in the embodiment shown, the dispensing section 16 is defined by substantially straight surfaces in the longitudinal direction of the nozzle 10, it is also contemplated to utilize curved surfaces or to include other wall structures or features. For example, a series of stepped surfaces can create a similar overall taper of dispensing section 16. A series of pleats could be utilized to create a positionable tip 18 that may adjustable to allow access to otherwise difficult to reach dental preparation sites.

As noted above, the choice of material may also be made (in addition to or instead of any such feature) to facilitate such a function, i.e. to make the tip permanently or elastically deformable.

Nozzle 10 may be provided open through tip 18 by an outlet 21 or may be closed such that an opening must be created prior to dispensing. In the case of the latter, the tip 18 may have an extension or portion thereof that is to be cut off or removed to make an outlet 21 prior to dispensing. In either case, liquid material 27 can be dispensed from interior storage section 14a through interior dispensing section 16a for application at a preparation site, such as the application of liquid dental material to the surface of a tooth. Tip exterior 18b is preferably spherical and also preferably includes a liquid application mechanism by which liquid material 27 can be applied. The liquid application mechanism has the capability to retain or suspend a small quantity of liquid at and at least partially about the tip exterior 18b after it has been dispensed through the outlet 21 so that the liquid can be applied to a preparation site. The liquid application mechanism also advantageously disperses liquid material within itself and about at least some of the surface area of the tip 18 for application of liquid material by a greater portion of the tip 18 than just its outlet 21. Where the tip 18 is substantially spherical, such as is illustrated, the liquid application mechanism preferably follows at least part of, and preferably as much as possible, of the spherical surface of tip 18 about the outlet 21. This can maximize the tip surface area that is usable to apply liquid material to a preparation sits. The liquid application material is fed the liquid material from the outlet 21. More than one outlet 21 can be provided connected to a common or discrete passages for supply.

In the embodiment shown in FIGS. 1 and 2, the liquid application mechanism comprises a plurality of small, flocked fibers 22 extending substantially radially from the spherical tip exterior 18b. The spherical tip exterior 18b having the flocked fibers 22 is beneficial for applying liquid dental material to the surface of a tooth, and in particular for applying such liquid material within a cavity prepared in a tooth, i.e. to fit within the prepared cavity. This ability may also be modified by the length of the flocked fibers 22. A flocked fiber tip can be made by any known or developed technique, such as is done in making the flocked tip disposable applicators that are commercially available from Microbrush Corporation of Clearwater, Fla. under the trade designation "Microbrush." The flocked fibers 22 define small interstitial spaces that can advantageously fill with liquid material, retain and suspend a small amount of liquid material 27 after it has been dispensed from outlet 21 to provide for efficient application to a preparation site. The fibers 22 also allow relatively uniform application of the liquid material over the surface(s) of the preparation site, whether irregular, rough, or smooth, and apply liquid material 27 in the same way as a brush would. In a tooth cavity, the radially extending fibers 22 from a spherical tip exterior 18b permit liquid dental material to be applied easily to side and overhang surfaces of the tooth cavity as well as the cavity bottom.

It is also contemplated that the liquid application mechanism be formed in other ways and be comprised of other materials. Bristles can be secured at the tip 18 in any conventional or developed way, but should be arranged to disperse and suspend liquid material in accordance with the present invention. The bristles may be conventional in the sense of those that are suitable for paint brush type applicators. Another type of liquid application mechanism would be a liquid dispersing material, such as an open cell foam or woven or nonwoven fabrics such as felt (e.g. as used in felt tip markers), covering at least a part of the tip 18. Liquid could enter the open cell foam or other material from the outlet 21 and disperse therein for application. That is, as with the flocked fibers and brushes noted above, such other materials should preferably be able to retain or suspend a small quantity of liquid outside of the nozzle tip 18 to facilitate application by more than just the tip outlet 21. Resilient mechanisms (made up of multiple elements like fibers or bristles or of liquid dispersing material like open cell foam) are preferred in that they have the added ability to conform and apply liquid material to an irregular surface. Moreover, multiple mechanisms can be used together to cover various portions of a tip or in combination over one another.

To effectively dispense some of or the complete quantity of the liquid material 27 through outlet 21, nozzle 10 can include a piston 23 as illustrated in FIG. 2 that is provided within the interior storage section 14a. The inner surface defining the interior storage section 14a also provides a guide surface for guiding the movement of the piston 23 from its initial position to a fully dispensed position. Piston 23 is preferably sized and shaped to be movable within the interior storage section 14a and to form a substantially liquid-tight seal throughout this movement so that substantial leakage of liquid material around the piston 23 is minimized during dispensing. Although the piston 23 may comprise any material usable for this purpose and compatible with the liquid material to be dispensed, elastomeric material is preferred. For reasons discussed below, piston 23 preferably includes a cone-shaped indentation 25 on the rear face thereof, that is, the face of piston 23 not in contact with the liquid dental material 27. Pressure applied to the rear face of piston 23 causes piston 23 to move down along the interior storage section 14a to force the liquid material through the dispensing section 16 and ultimately to dispense liquid material 27 through outlet 21 to be retained outside tip 18 within the liquid application mechanism. In order to make it easy for a user to tell when a nozzle 10 has been used, the section 14a could be made, coated or otherwise treated to be a different color. Then, movement of the piston 23 and evacuation of some of the liquid material would reveal a color change of that section.

As noted above, dispensing nozzle 10 is particularly designed for storage of liquid dental material and subsequent dispensing and application thereof at a preparation site of a patients teeth, gums or mouth. Nozzle 10 is preferably sized to allow for storage of an amount of liquid dental material required for one typical application to a patient. This may also be preferred in many other types of applications.

As shown in FIG. 2, liquid material 27 is stored in dispensing nozzle 10 and primarily occupies the interior storage section 14a. Although not necessary, an air pocket at tip interior 18a and a portion of interior dispensing section 16a is void of liquid material during storage. This ability depends largely on the viscosity of the liquid material and the manner by which the nozzles 10 are filled with the liquid material 27. This manner of filling may be any conventional or developed technique. When liquid material 27 is to be dispensed, such as by using drivers as described below, piston 23 forces the liquid material 27 from the interior storage section 14a, through the interior dispensing section 16a and tip interior 18a, and out of the nozzle 10 through the outlet 21. The liquid material can then be applied by virtue of the liquid application mechanism, such as the flocked fibers 22, onto a tooth surface or other preparation site.

The present invention also relates to a packaging construction for effectively capping one or more nozzles 10 for storage of liquid material 27 as it is contained within the nozzles 10. As is the case with some liquid dental materials, preferably the nozzles 10 are to be capped so as to limit the evaporation of solvents from the liquid material. FIG. 3 is a perspective view of a packaging construction that permits plural nozzles 10 to be filled and stored as an array and which effectively caps the plural nozzles 10 in accordance with the present invention. The packaging construction preferably includes a storage block 30 having a plurality of cavities 32 formed within the storage block 30 from a top surface 31 thereof. Each cavity 32 is sized to accommodate a single dispensing nozzle 10, which is placed into a cavity 32 in a tip-first orientation. Block 10 is preferably formed of plastic or other similar polymeric material, such as polypropylene, but may also be formed of other materials depending on any particular application. Moreover, various types of surface treatments may be provided to the block material, such as for example metalizing. In any case, it is preferable that the block exhibit low permeability to solvents and high permeability to oxygen. Preferably, the material and any coatings or treatments are chosen so that it, by the portions of the storage block 30 described below, will create, with portions of the nozzles 10, effective seals. Otherwise, the storage block 30 may be shaped and sized to accommodate any number of nozzles 10 and to position the nozzles in any desired manner. That is, the nozzles 10 need not be arranged in an array, or from a single surface (planar or not) of the storage block 30. Where the nozzles 10 have closed tips 18, as contemplated above, that must be opened prior to dispensing, the storage block 30 could be provided with a cutting mechanism (not shown) for cutting tips 18 at a controlled depth to provide outlets 21 through the tips 18 prior to use.

The design and relative dimensions of storage block 30 and nozzles 10 are preferably chosen to allow storage block 30 and nozzle 10 to be used both for filling a plurality of nozzles 10 with liquid material 27 and for storing of the liquid material within the nozzles 10 for an extended period of time. As shown in FIG. 4, which is a sectional view of storage block 30 taken along section line 4—4 of FIG. 3, each cavity 32 preferably has a relatively wider outer bore portion 34 which steps down to a relatively narrower inner bore portion 36. The transition between the outer and inner bore portions may be abrupt or gradual and may be defined by any number of straight or curved surfaces as viewed in cross-section. Both the outer and inner bore portions 34 and 36 of each cavity 32 are preferably generally cylindrical to accommodate the shape of nozzles 10. However, if nozzles 10 are differently shaped, then the cavities 32 may also be otherwise shaped to allow a tight fit between at least a portion of each cavity 32 and a portion of the exterior surface of a nozzle 10 when a nozzle 10 is positioned in a cavity 32. Moreover, the outer and inner bore portions 34 and 36 may be made by any conventional process and may not be uniform along their respective lengths.

The diameter of the outer bore portion 34, particularly at a mouth 38 thereof, is preferably substantially the same as the outside diameter of the exterior storage section 14b of nozzle 10 directly beneath shoulder 24. Also, the diameter of inner bore portion 36 is preferably such that an upper edge thereof will contact the surface of the exterior dispensing section 16b somewhere intermediate of the tip 18 and the liquid storage section 14. This dimension may actually be slightly smaller if the material of the nozzle section 16 is elastically or plastically deformable under the applied force. This can enhance the contact to create a better seal, as described below. Inner bore portion 36 is also wide enough to allow tip 18, including the liquid application mechanism, such as flocked fibers 22, to fit inside the inner bore portion 36 without crushing or substantially distorting the liquid application mechanism. Further, the total depth of the cavities 32 preferably allows tips 18 to be suspended above a bottom 40 of each cavity 32 when a nozzle 10 is inserted completely therein, i.e. up to its shoulder 24.

These relative dimensions allow for an overall seal to be created from approximately the inlet 20 to the outlet 21 as shown in FIG. 4 for tip 18 when a dispensing nozzle 10 is placed in a cavity 32 to prevent excessive evaporation of solvents from the liquid material 27. To provide this overall seal, two individual seals are created according to this embodiment between storage block 30 and nozzle 10. First, because the outer diameter of exterior storage section 14b just below shoulder 24 is preferably substantially the same as the inner diameter of mouth 38 of a cavity 32, shoulder 24 extends beyond mouth 38 to form a first seal when nozzle 10 is placed in cavity 32. A tight fit along the remainder of the exterior storage portion 14b and the surface of the outer bore portion 34 enhances this first seal. The extension of the shoulder 24 onto the surface 31 around the mouth 38 can be minimal depending on the materials of the nozzle 10 and the storage block 30. Second, when dispensing section 16 is positioned within the inner bore portion 36 of cavity 32, a mouth 42 of inner bore portion 36 will contact and preferably pinch an intermediate portion of the exterior dispensing section 16b. This creates a second seal for tip 18. The combination of these first and second seals provides an overall seal to prevent excessive evaporation of solvents from the liquid material 27 between the exterior of a cavity 32 and the inner bore portion 36 where tip 18 is housed.

The overall seal provided by each cavity 32 of storage block 30 allows a plurality of dispensing nozzles 10 to be filled with liquid material 27 in storage block 30. To fill a plurality of nozzles 10 with liquid material 27, storage block 30 can be populated with dispensing nozzles 10. Nozzles 10 can then be filled either conventionally or otherwise with liquid material 27. Because all the nozzles 10 in a single storage block 30 can be handled in one large group instead of individually, the nozzles 10 may be filled with multiple dosing heads. That is, dosing heads that will fill multiple nozzles at once. Because of the overall seal between outlet 21 and an exterior of cavity 32, as each dispensing nozzle 10 is being filled with dental material 27, a substantial airlock is created in the interior region of cavity 32 surrounding each dispensing nozzle 10. This airlock will prevent sufficiently viscous liquid dental material 27 from passing through each outlet 21 and into each cavity 32. Indeed, as shown in FIGS. 2 and 4, due to the airlock, liquid material 27 generally does not even fill the interior dispensing section 16a of nozzle 10 but mainly fills interior storage section 14a thereof. After filling the nozzles 10 as positioned by the storage block 30, pistons 23 can be loaded into interior storage sections 14a of nozzles 10.

Seals 19 may then be adhered to inlets 20 of nozzles 10 at flange sections 12 to provide a seal at each inlet 20. Alternatively, all or some of the nozzles 10 may be sealed at their inlets 20 by the same sealing material. That is, any number of the inlets 20 can be covered and bonded to a same layer of sealing material.

Shoulder 24 of each nozzle 10 also advantageously positions the flange section 12 of each nozzle 10 above the surface 31 of block 30. As a result, the flange section 12 can be connected to a driver (as detailed below), such as by lateral movement of the driver, without first having to lift a nozzle 10 from the block 30. That is, the flange section 12 is positioned so that the nozzle 10 can be easily picked directly from the block 30.

It is also contemplated that the nozzles 10 in accordance with the present invention may be packaged individually or otherwise in multiple quantities. A storage block 30 packaging construction is beneficial for all of the reasons set out above. But, if those advantages are not needed or desired, any number of caps or sealing techniques can be used for one or more of the nozzles 10. For example, a cap having but a single cavity with an interior shaped and sized like the interior of cavity 32 described above could be used to individually cap a nozzle 10.

As noted in the Background section, many liquid dental materials contain solvents such as ethanol which, if allowed to evaporate, can render the liquid dental material less effective and/or un-useable. Thus, a packaging construction for such liquid dental material should provide for an appropriate shelf life. Without limitation, the following liquid dental materials contain solvents which would be expected to benefit from the advantages of the nozzle and packaging construction of the present invention: the bonding system available under the trade designation "Gluma 2000" from Bayer A. G. of Germany; the adhesive system available under the trade designation "One-Step" from Bisco, Inc. of Schaumburg, Ill.; and the "Prime & Bond" Direct Composite Bonding Agent from Dentsply International, Inc. of York, Pa.

Figure 7:
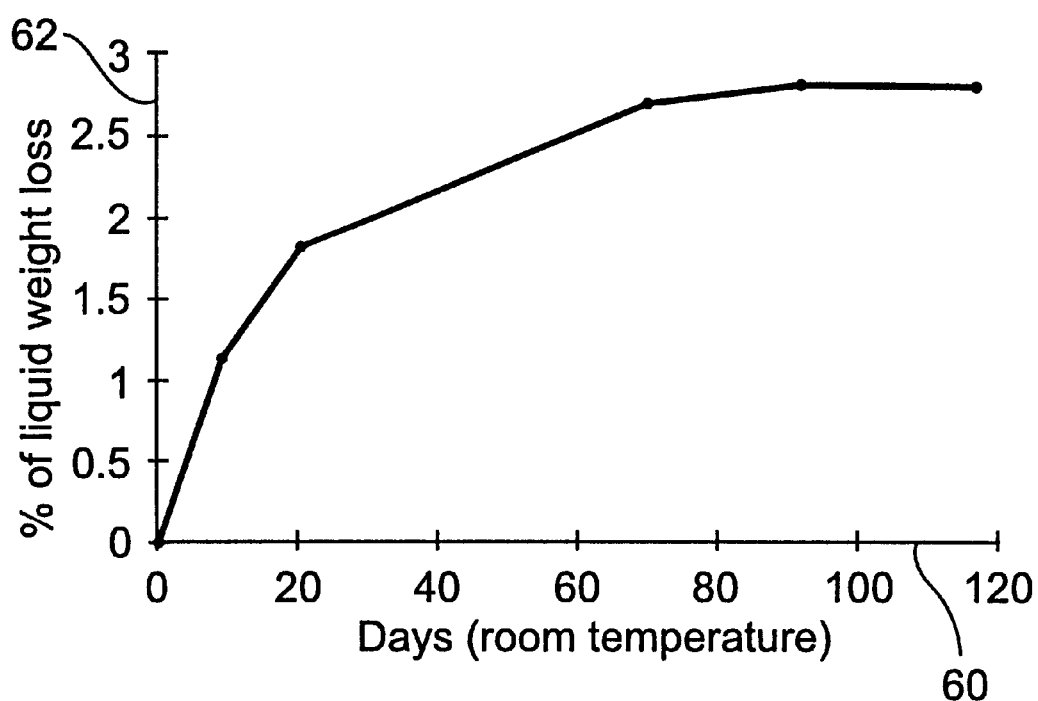
FIG. 7 is a graph comparing the number of days of storage of liquid dental material in a nozzle and package block system of the present invention versus the percentage of liquid weight loss of the liquid dental material.

To ensure an appropriate shelf life, the overall seal created by the packaging construction of the present invention between an outlet 21 of a nozzle 10 as positioned within a cavity 32 and the exterior of cavity 32 acts to prevent substantial evaporation of such solvents. Thus, this overall seal allows relatively long term storage of liquid dental material as provided within nozzles 10 and as packaged by a storage block 30. To evidence this ability, dispensing nozzles substantially the same as nozzle 10 described above were placed in packaging constructions substantially the same as storage block 30. As positioned within a polypropylene storage block to create the sealing mechanisms described above, polypropylene nozzles were filled with liquid dental material having ethanol as a solvent. Specifically, the liquid dental material was the dental adhesive available from Minnesota Mining & Manufacturing Company of St. Paul, Minn. under the trade designation "3M Single Bond." Twelve nozzles were each filled with 0.03 g of such material. The inlets of the nozzles were then sealed using a foil material as the seal 19, described above. The nozzles were weighed at various intervals over a period of 120 days of storage at room temperature. The results of the tests are shown in FIG. 7, which is a graph plotting the results comparing the days in storage on the x-axis 60 versus the percent of liquid weight loss on axis 62.

As shown, while there was an initial weight loss of about 1% to 2% over the first 20 to 40 days, but after about 80 days, the weight loss plateaued at between 2.5% and 3%. It is thought that this weight loss was mainly due to evaporation of solvent into the airlock, described above, between the bottom of the liquid in the dispensing areas of the tested nozzles and the exterior of the storage block. A weight loss of 2.5% to 3% is deemed very acceptable. Indeed, the samples of dental adhesive were tested for adhesion after the 120 days and found to display statistically the same adhesion as new material.

Figure 5:
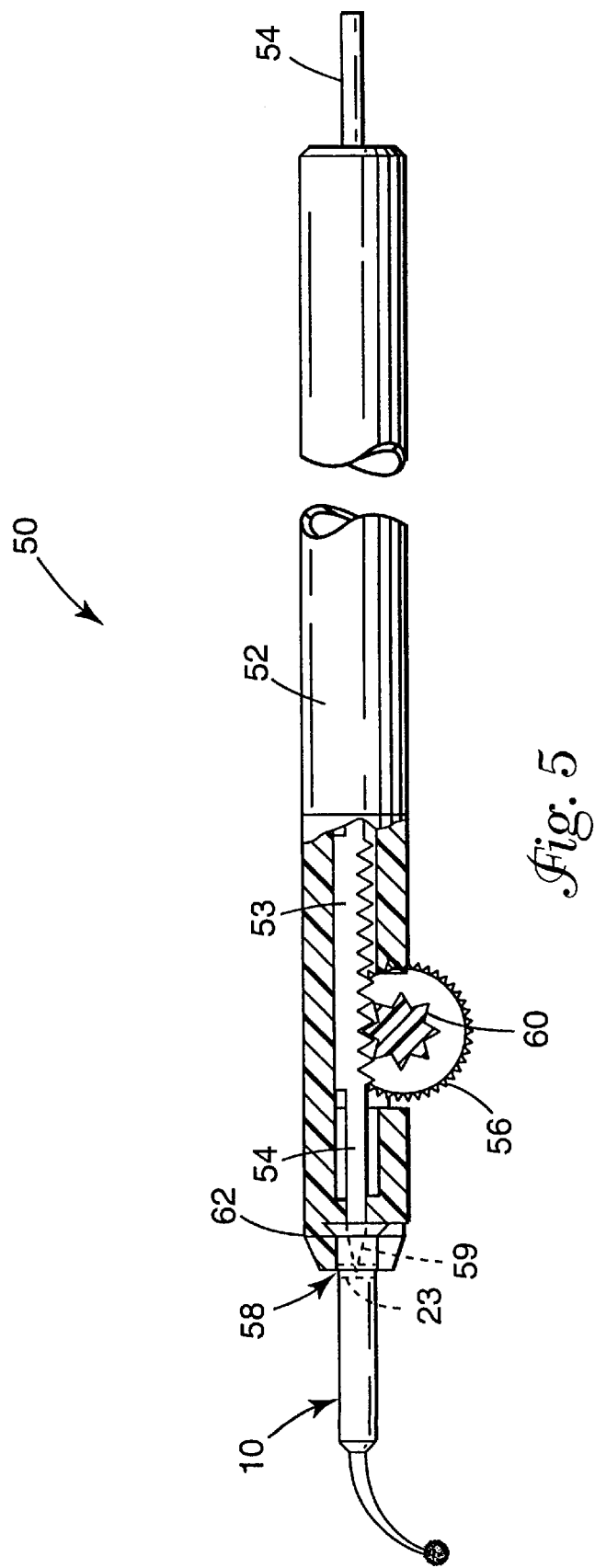
FIG. 5 is a partially cut away side view of a driver having a nozzle as shown in FIG. 1 attached to one end thereof.

To apply liquid material 27 that is stored in a nozzle 10 to a preparation site, such as a tooth, a driver such as the driver 50 shown in FIG. 5 can be used. Such driver devices are commercially available from DMG GmbH in Germany under the trade designation "Ecu-PEN." The illustrated driver 50 includes a hollow shaft 52, a plunger 54 having an integral rack portion 53 and a geared wheel 56. The rack portion 53 of plunger 54 is positioned concentrically inside shaft 52 to allow plunger 54 to extend through an aperture 58 in one end of driver 50. Geared wheel 56 is fixed in position to be rotatable by a wall of shaft 52 and includes a round gear 60 which engages the rack portion 53 of plunger 54 so that rotation of the geared wheel 56, such as by a users finger, causes plunger 54 to extend or retract through aperture 58, depending upon the direction of rotation of geared wheel 56. The driver 50 as commercially available is preferably modified to have a pointed tip such as shown at 59 in FIG. 5 for puncturing the seal 19, if provided, and to drive the piston 23 within the nozzle 10 for dispensing.

To use the driver 50 with a nozzle 10 to dispense liquid material 27, a nozzle 10 is attached to the end of driver 50 having aperture 58. To facilitate this attachment, driver 50 preferably includes a tip having a cutout 62 that permits a nozzle 10 to be loaded onto the driver 50 by relative radial movement and which longitudinally fixes the nozzle 10 in position with the driver 50. Cutout 62 is provided at one side of the driver 50 adjacent to the aperture 58 and is sized to permit the flange section 12 and a portion of the section 14 of nozzle 10 to pass radially therethrough by lateral relative movement. The aperture 58 is sized for positioning the inlet 20 of nozzle 10 in alignment with the plunger 54. Further, the cutout 62 is slightly smaller than the respective sizes of the relevant nozzle sections so that the nozzle 10 can be snap fit through the cutout 62 to attach nozzle 10 to driver 50. The necessary resiliency for this snap fit is primarily provided by the nozzle 10 so that it can slightly elastically deform as it is loaded in position. Snap-fitting a nozzle 10, as positioned by the cooperation of nozzle shoulders 24 and the surface 31 of a storage block 30, onto a driver 50 in this way can be accomplished with a single hand, without having to touch nozzle 10 or first remove it from storage block 30, and with gloves on. It is also contemplated to attach a nozzle 10 to driver 50 in other ways such as by a threaded connection, a bayonet-type coupling or a coupling similar to a Luer fitting or the like.

Once a nozzle 10 is attached to driver 50, nozzle 10 can be removed from storage block 30 to break the overall seal. To cause dispensing of liquid material, the geared wheel 56 of driver 50 can be rotated to extend plunger 54. As shown in FIG. 5, the pointed tip 59 of plunger 54 is extended with the plunger 54 so that when the pointed tip 59 is sufficiently extended from driver 50, it will puncture the seal 19 over the inlet 20 of nozzle 10. As plunger 54 is extended farther from the aperture 58 of the driver 50, it will engage piston 23 at its cone-shaped indentation 25 to force piston 23 to move as guided by the interior storage section 14a of nozzle 10. As explained above, this will cause liquid material 27 that is stored within nozzle 10 to be dispensed from outlet 21 of tip 18 and to allow application at a preparation site.

Figure 6:
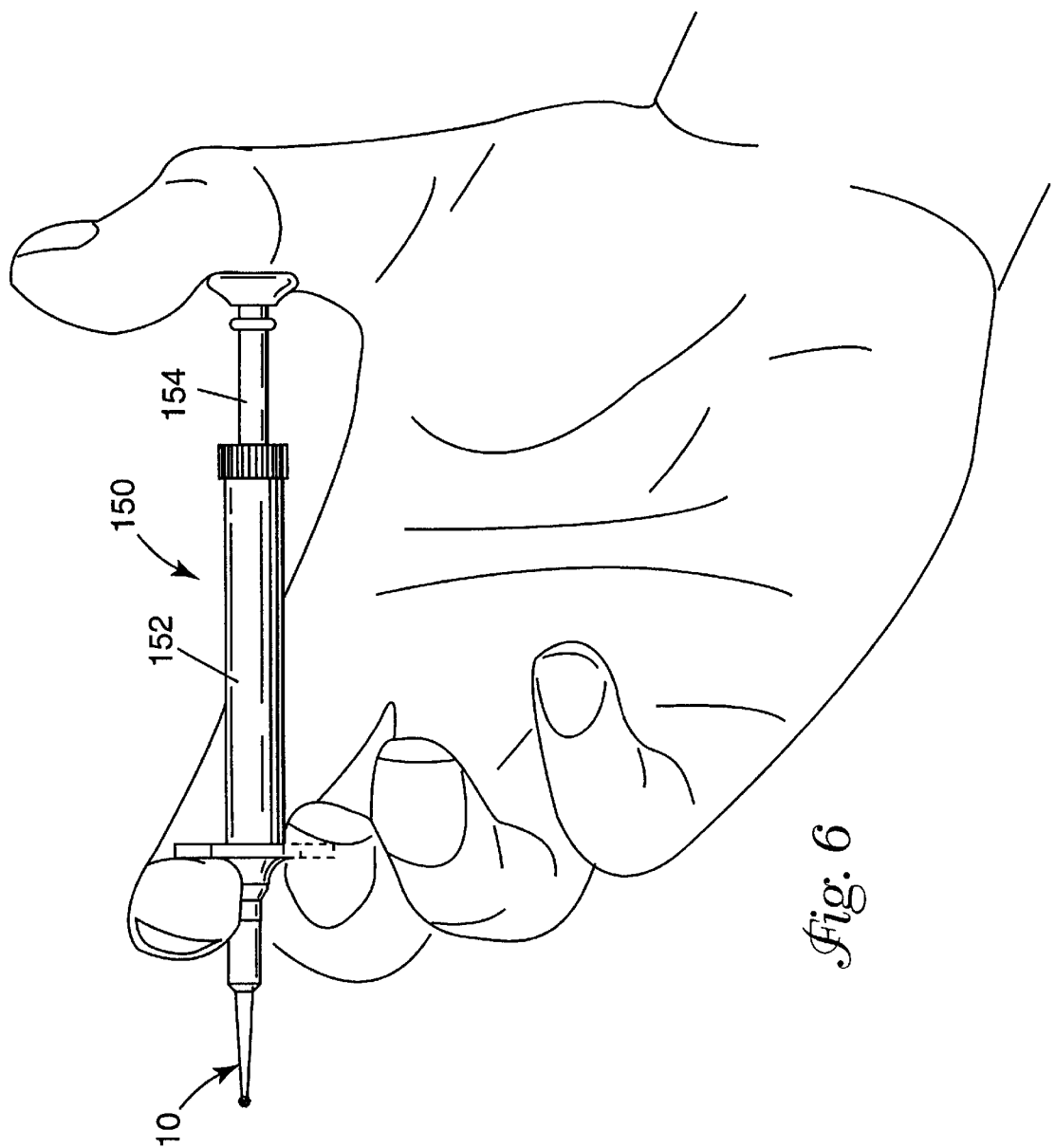
FIG. 6 is a side view of a second embodiment of a driver combined with a nozzle as shown in FIG. 1 as positioned for dispensing and applying by a user.

It is contemplated that a driver, such as driver 50, for applying liquid material from nozzle 10 to a preparation site can be any device having a plunger, such as plunger 54, which can enter nozzle 10 to cause liquid material 27 to be dispensed from outlet 21. A second embodiment of such a driver is shown in FIG. 6, which is a side view of a driver 150 as held by a user. Driver 150 is a syringe type applicator, such as described in U.S. Pat. No. 5,626,473 to Mühlbauer et al., the entire disclosure of which is incorporated herein by reference. A hollow shaft 152 contains and guides a spring loaded plunger 154. By applying pressure to one end of plunger 154 against the force of its spring bias, its other end is moved down the interior of shaft 152 and into the inlet 20 of nozzle 10. As above, the other end of the plunger can be pointed to puncture a seal 19 of a nozzle 10. The remainder of the dispensing and applying process would be the same as described above.

Use of a nozzle 10 for storing, dispensing and applying liquid material to a preparation site has a number of advantages over prior art mechanisms for storing and dispensing liquid material as described above in the Background section. Moreover the use of a storage block 30 provides its own advantages that can be added to that of the inventive nozzle 10. The chance of spillage is reduced because the driver 50 can be attached directly to nozzle 10 without lifting or otherwise removing nozzle 10 from storage block 30. And, once driver 50 is attached to nozzle 10, a user must actively move plunger 54 forward into nozzle 10 to cause liquid material to dispense. Also, the entire application procedure including removing a nozzle 10 from storage, attaching nozzle 10 to a driver, unsealing nozzle 10 and applying liquid material to a preparation site can take place easily by using one hand even with gloves on. This leaves, for example, a dental professional's other hand free, which can be important in the performance of dental procedures. Further, because driver 50 can be directly attached to nozzle 10 while nozzle 10 is still in storage block 30, the procedure can be considered "no-touch." This reduces the likelihood of contamination or contact of the dental material or the nozzle tip 18 with the dental professional's skin or gloves.

For dental applications, setup time can also be reduced because there is no need to pre-measure a given amount of dental material from a bulk vial into a well; the amount of liquid in each nozzle 10 in a storage block 30 is preferably pre-measured to be approximately a unit dose, i.e. the correct amount for a single use on a patient. Cleanup can also be relatively quick because after use, the nozzles 10 can be either replaced back into storage block 30 for disposal or disposed of directly. Also, the only item which requires disinfection is the driver 50. Additionally, the determination of how many applications of dental material remain before material must be re-supplied is relatively simple. It is only necessary to count the nozzles remaining in a storage block 30, and/or the number of blocks 30 remaining. Because nozzle 10 provides a supply of liquid dental material via outlet 21 of tip 18 to the liquid application mechanism, there is no need to remove nozzle 10 from a patients mouth to re-apply liquid dental material by the liquid application mechanism of the tip 18. This can reduce the possibility of drippage from tip 18 and save time in applying dental material to a preparation site. Furthermore, because a plurality of nozzles 10 can be filled and stored in storage block 30 in relatively close proximity, use of the present invention can provide for relatively efficient use of space.

As noted throughout this case, the storing, dispensing and applying device of the present invention can be used for all sorts of liquid materials. For example, any type of adhesive application would benefit from the inventive nozzle design. Moreover, the packaging construction is likewise applicable to any such liquids, but in particular where it is desirable to facilitate handling (i.e. loading and unloading of nozzles) without touching the nozzles and where a sealing arrangement is desired.

Though the present invention has been described with reference to preferred embodiments, those skilled in the art will recognize that changes can be made in form and detail without departing from the spirit and scope of the invention.

What is claimed is:

1. A nozzle for storing therein a quantity of liquid material and for attachment to a driver so that the liquid material can be dispensed and applied to a preparation site, the nozzle having a passage defined from an inlet at one end thereof to an outlet at a tip on another end thereof, the inlet providing access to the passage within the nozzle for a driver device when attached to a driver, the passage sized for containing a predetermined quantity of liquid material, and the outlet permitting dispensing of liquid material from the passage, wherein the nozzle further comprises a liquid application mechanism that includes a liquid retaining structure that extends outwardly from a surface provided at the tip within which liquid material that is to be provided through the outlet can be dispersed and retained over at least a portion of the surface of the tip that is located adjacent to the outlet so that liquid material can be applied to a preparation site by a surface area of the tip that is greater than an opening area of the outlet;

and the nozzle in combination with a packing construction comprising a storage block having a cylindrical cavity within which the nozzle is removably positioned so as to create an overall seal surrounding the passage from approximately the inlet to the outlet.

2. The nozzle of claim 1, wherein the nozzle includes a seal at the inlet end of the nozzle.

3. The nozzle of claim 2, wherein the seal is made of a foil/film laminate that is heat sealed to the inlet of the nozzle.

4. The nozzle of claim 1, wherein the liquid retaining structure of the liquid application mechanism includes fibers flocked onto and substantially radially extending from a spherical portion of the tip about the outlet.

5. The combination of claim 1, wherein the packaging device includes a storage block having a plurality of cavities formed therein, and plural nozzles are supported by the storage block.

6. The combination of claim 5, wherein the nozzles each include a shoulder between their inlet and outlet ends that extends from each nozzle to abut the storage block and limit an inward position of each nozzle within a cavity of the storage block.

7. The combination of claim 1, wherein the cavity is sized and shaped so that an inner portion of the storage block within the cavity is in contact with an intermediate external surface portion of the nozzle so as to form a first seal.

8. The combination of claim 7, wherein the cavity also is sized so that an outer portion of the storage block within the cavity is in contact with another external surface portion of the nozzle that is closer to the inlet than the intermediate external surface portion thereof so as to form a second seal.

9. The combination of claim 8, wherein the cavity is defined by an outer bore portion and an inner bore portion, the outer bore portion providing a larger opening through a surface of the storage block than an opening into the inner bore portion within the cavity, and the opening into the inner bore portion is defined by the inner portion of the storage block that provides the first seal with the nozzle.

10. The combination of claim 9, wherein the nozzle further includes a shoulder extending along the external perimeter of the external surface portion of the nozzle that forms at least part of the second seal, and the shoulder is dimensioned to contact the surface of the storage block about which the opening is provided by the outer bore portion.

11. The combination of claim 9, wherein the liquid-application mechanism includes fibers flocked onto the tip about the outlet and the inner bore portion of the cavity is sized and shaped to allow the nozzle tip to be positioned therein without crushing the fibers flocked onto the nozzle tip.

12. The nozzle of claim 1 in combination with a driver, the driver including a guide device having an attachment means releasably connected with the nozzle, the driver also including a plunger slidably disposed within the guide device, the plunger being movable along a length of the guide device and extendible from an end of the guide device and into the inlet of the nozzle as positioned by the attachment means.

13. The combination of claim 12, further in combination with a predetermined quantity of liquid dental material provided within the passage of the nozzle and a piston slidably disposed within the passage of the nozzle between the quantity of liquid dental material and the inlet, the piston having a surface thereof for engagement with the plunger of the driver so that extension of the plunger into and partially through the passage of the nozzle will cause the piston to move the quantity of liquid dental material within the passage toward the outlet.

14. The combination of claim 13, wherein the nozzle includes a seal at the inlet end of the nozzle and the plunger of the driver has a pointed tip so that when the nozzle is attached to the driver and the plunger is extended sufficiently from an end of the guide device of the driver, the pointed tip of the plunger will puncture the seal.

15. The nozzle of claim 1, in combination with a predetermined quantity of liquid dental material provided within the passage of the nozzle and a piston slidably disposed within the passage of the nozzle between the quantity of liquid dental material and the inlet, the piston having a surface positioned to engage with a driver device of a driver when attached thereto so that the driver device can cause the piston to move the quantity of liquid dental material within the passage toward the outlet.

16. A package construction for a plurality of nozzles having a predetermined quantity of liquid material stored therein, the package construction comprising:
a plurality of nozzles having therein a quantity of liquid material and having a means for attachment to a driver so that the liquid material can be dispensed and applied to a preparation site, each nozzle having a passage defined from a sealed inlet at one end thereof to a tip on another end thereof, the inlet providing access when its seal is opened to the passage within the nozzle for a driver device when attached to a driver, the passage sized for containing the predetermined quantity of liquid material, and the outlet permitting dispensing of liquid material from the passage,
a storage block having an external surface with plural openings that provide access to a plurality of cavities that extend within a depth of the storage block within which a plurality of the nozzles are provided with their respective attachment means accessible for connection to a driver without first removing the nozzles from the storage block, said nozzles being unattached to a driver and removably positioned within the cavities so as to create an overall effective seal therewith so as to allow the liquid material to be stored in the passages of the unattached nozzles for a relatively extended period of time.

17. The packaging construction of claim 16, wherein the nozzles each include an outlet at their tip so that each nozzle is open within a cavity of the storage block.

18. The packaging construction of claim 17, wherein the nozzles each include a liquid application mechanism that comprises a liquid retaining structure extending outwardly from a surface provided at their tip within which liquid dental material, that comprises the liquid material within the nozzles provided from within a nozzle through its outlet, can be dispersed over at least a portion of the surface of the tip that is located adjacent to the outlet so that liquid dental material can be applied to a preparation site by a surface area of the tip that is greater than an opening area of the outlet.

19. The packaging construction of claim 18, wherein the liquid retaining structure of the liquid application mechanism of each nozzle comprises fibers flocked onto and substantially radially extending from a spherical portion of the nozzle tip.

20. The packaging construction of claim 17, wherein each cavity is sized and shaped so that an inner portion of the storage block within each cavity is in contact with an intermediate external surface portion of a nozzle so as to form a first seal.

21. The packaging construction of claim 20, wherein each cavity also is sized so that an outer portion of the storage block within each cavity is in contact with another external surface portion of a nozzle that is closer to the inlet than the intermediate external surface portion thereof so as to form a second seal.

22. The packaging construction of claim 21, wherein each cavity is defined by an outer bore portion that extends within the depth of the storage block and an inner bore portion that extends in substantial alignment with the outer bore portion and further within the depth of the storage block from the outer bore portion so as to effectively position the nozzle attachment means for access by a driver, the outer bore portion providing a larger opening through a surface of the storage block than an opening into the inner bore portion within the cavity, and the opening into the inner bore portion is defined by the inner portion of the storage block that provides the first seal with a nozzle.

23. The packaging construction of claim 22, wherein each nozzle further includes a shoulder extending along the external perimeter of the external surface portion of the nozzle that forms at least part of the second seal, and the shoulder is dimensioned to contact the surface of the storage block about which the opening is provided by the outer bore portion of its respective cavity.

24. The packaging construction of claim 23, wherein each nozzle includes a liquid application mechanism that comprises a liquid retaining structure extending outwardly from a surface provided at their tip within which liquid dental material, that comprises the liquid material within the nozzles provided from within a nozzle through its outlet, can be applied to a dental preparation site and which facilitates dispersion of liquid dental material from within a nozzle over at least a portion of the surface of the nozzle tip during application of liquid dental material to a dental preparation site, the liquid retaining structure of the liquid application mechanism of each nozzle comprising fibers flocked onto and substantially radially extending from a spherical portion of the nozzle tip, and the inner bore portion of each cavity is sized and shaped to allow a nozzle tip to be positioned therein without crushing the fibers flocked onto and extending from the nozzle tip.

25. A package construction for a plurality of nozzles for containing a predetermined quantity of liquid material therein, the package construction comprising:
a plurality of nozzles having therein a quantity of liquid material and having a means for attachment to a driver so that the liquid material can be dispensed and applied to a preparation site, each nozzle having a passage defined from a sealed inlet at one end thereof to a tip on another end thereof, the inlet providing access when its seal is opened to the passage within the nozzle for a driver device when attached to a driver, the passage sized for containing the predetermined quantity of liquid material, and the outlet permitting dispensing of liquid material from the passage, each nozzle also having a shoulder between their inlet and outlet ends that extends from each nozzle;

a storage block having an external surface with plural openings that provide access to a plurality of cavities that extend within a depth of the storage block within which a plurality of the nozzles are provided with their respective attachment means accessible for connection to a driver without first removing the nozzles from the storage block, said nozzles being unattached to a driver and removably supported within the cavities as positioned by the shoulder of each unattached nozzle that limits an inward position of each unattached nozzle within a cavity of the storage block by abutment of the shoulder of an unattached nozzle with a surface of the storage block.

26. The package construction of claim 25, wherein the nozzles are removably positioned within the cavities of the storage block so as to create an overall effective seal therewith so as to allow the liquid material to be stored in the passages of the nozzles for a relatively extended period of time.

27. The packaging construction of claim 26, wherein the nozzles each include an outlet at their tip so that each nozzle is open within a cavity of the storage block.

28. The packaging construction of claim 27, wherein the nozzles each include a liquid application mechanism that comprises a liquid retaining structure extending outwardly from a surface provided at their tip within which liquid dental material, that comprises the liquid material within the nozzles provided from within a nozzle through its outlet, can be dispersed over at least a portion of the surface of the tip that is located adjacent to the outlet so that liquid dental material can be applied to a preparation site by a surface area of the tip that is greater than an opening area of the outlet.

29. The packaging construction of claim 28, wherein the liquid retaining structure of the liquid application mechanism of each nozzle comprises fibers flocked onto and substantially radially extending from a spherical portion of the nozzle tip.

30. The packaging construction of claim 27, wherein each cavity is sized and shaped so that an inner portion of the storage block within each cavity is in contact with an intermediate external surface portion of a nozzle so as to form a first seal.

31. The packaging construction of claim 30, wherein each cavity also is sized so that an outer portion of the storage block within each cavity is in contact with another external surface portion of a nozzle that is closer to the inlet than the intermediate external surface portion thereof so as to form a second seal.

32. The packaging construction of claim 31, wherein each cavity is defined by an outer bore portion that extends within the depth of the storage block and an inner bore portion that extends in substantial alignment with the outer bore portion and further within the depth of the storage block from the outer bore portion so as to effectively position the nozzle attachment means for access by a driver, the outer bore portion providing a larger opening through a surface of the storage block than an opening into the inner bore portion within the cavity, and the opening into the inner bore portion is defined by the inner portion of the storage block that provides the first seal with a nozzle.

33. The packaging construction of claim 32, wherein the shoulder of each nozzle extends along an external perimeter of the external surface portion of the nozzle that forms at least part of the second seal, and the shoulder is dimensioned to contact the surface of the storage block about which the opening is provided by the outer bore portion of its respective cavity.

34. The packaging construction of claim 33, wherein each nozzle includes a liquid application mechanism that comprises a liquid retaining structure extending outwardly from a surface provided at their tip within which liquid dental material, that comprises the liquid material within the nozzles provided from within a nozzle through its outlet, can be applied to a dental preparation site and which facilitates dispersion of liquid dental material from within a nozzle over at least the surface portion of the nozzle tip during application of liquid dental material to a dental preparation site, the liquid retaining structure of the liquid application mechanism of each nozzle comprising fibers flocked onto and substantially radially extending from a spherical portion of the nozzle tip, and the inner bore portion of each cavity is sized and shaped to allow a nozzle tip to be positioned therein without crushing the fibers flocked onto and extending from the nozzle tip.

* * * * *